United States Patent [19]

Vaughan

[11] 4,110,353
[45] Aug. 29, 1978

[54] PROCESS FOR THE PRODUCTION OF TETRAHYDROANTHRAQUINONES

[75] Inventor: Lawrence G. Vaughan, Wilmington, Del.

[73] Assignee: E. I. Du Pont de Nemours and Company, Wilmington, Del.

[21] Appl. No.: 858,664

[22] Filed: Dec. 8, 1977

Related U.S. Application Data

[63] Continuation-in-part of Ser. No. 417,804, Nov. 21, 1973.

[51] Int. Cl.² ............................................. C07C 49/68
[52] U.S. Cl. .................................................... 260/369
[58] Field of Search .......................................... 260/369

[56] References Cited

U.S. PATENT DOCUMENTS

| | | | |
|---|---|---|---|
| 2,072,867 | 3/1937 | Carothers | 260/369 X |
| 3,838,178 | 9/1974 | Vaughan | 260/369 |
| 3,888,890 | 6/1975 | Kirchner et al. | 260/369 |

FOREIGN PATENT DOCUMENTS 614,296  2/1961  Canada ...................................... 260/369

Primary Examiner—Allen B. Curtis
Assistant Examiner—Raymond Covington

[57] ABSTRACT

High yields of tetrahydroanthraquinones are obtained by oxidizing a compound of the formula

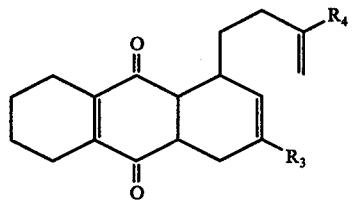

wherein $R_3$ and $R_4$ are the same or different and can be an alkyl group having one to eight carbon atoms or hydrogen. The reaction product thus produced is useful in the anthraquinone process for producing hydrogen peroxide.

16 Claims, No Drawings

PROCESS FOR THE PRODUCTION OF TETRAHYDROANTHRAQUINONES

CROSS REFERENCE TO RELATED APPLICATION

This application is a continuation-in-part of our co-pending application Ser. No. 417,804, filed Nov. 21, 1973.

BACKGROUND OF THE INVENTION

1. Field of Use

The process of this invention relates to the preparation of a 5,6,7,8-tetrahydro-1-alkenyl-9,10-anthraquinone by oxidizing the adduct of a triene and tetrahydronaphthaquinone in the presence of molecular oxygen, a strong organic base and optionally a solvent.

2. Prior Art

The use of alkylanthraquinones and/or their tetrahydro derivatives as working intermediates in cyclic reduction-oxidation processes for producing hydrogen peroxide is well known. In such processes, commonly referred to as anthraquinone processes, the working intermediate or mixture of two or more thereof is dissolved in a suitable water immiscible solvent or mixture of solvents and the solution is alternately reduced and oxidized. In the reduction stage, the working intermediate is hydrogenated in the presence of a suitable catalyst to reduce it to its anthrahydroquinone form. In the subsequent oxidation stage, the intermediate is reoxidized with molecular oxygen, e.g., in the form of air, to reform the anthraquinone and simultaneously produce hydrogen peroxide. The hydrogen peroxide is then removed from the working solution, generally by extraction with water, and the residual anthraquinone working solution is recycled to the reduction stage for a repetition of the cycle.

Canadian Pat. No. 614,296 issued to Ferri on Feb. 7, 1961, and the following U.S. patents (issue dates in parentheses) are representative of the many issued patents relating to anthraquinone processes for producing hydrogen peroxide: Reidl et al., U.S. Pat. Nos. 2,158,525 (5/16/39) and 2,215,883 (9/24/40); Dawsey et al., U.S. Pat. No. 2,537,655 (1/9/51); Sprauer, U.S. Pat. No. 2,657,980 (11/3/53); Harris et al., U.S. Pat. No. 2,668,753 (2/9/54) and Hinegardner, U.S. Pat. No. 2,689,169 (9/14/54) and Darbee et al., U.S. Pat. No. 3,062,622 (11/6/62); Hiratsuka et al., U.S. Pat. No. 3,038,786 (6/12/62); Dawsey, U.S. Pat. No. 3,041,143 (6/26/62); Kabisch, U.S. Pat. No. 3,328,128 (6/27/67); Kabisch et al., U.S. Pat. No. 3,488,150 (1/6/70) and Logan et al., U.S. Pat. No. 3,493,343 (2/3/70).

As is recognized in such issued patents, it is important in commercial operations that the working solution employed have a high hydrogen peroxide synthesis capacity per cycle and that the hydrogen peroxide solution obtained in the extraction step be relatively concentrated. The concentration of the hydrogen peroxide is determined largely by the solubility of the working intermediate employed, particularly in its anthrahydroquinone form. Certain tetrahydro-1-alkyl-anthraquinones which are disclosed in U.S. Pat. No. 3,888,890 and which exhibit outstanding solubilities in working solvents of the type commonly used are particularly well suited for use in cyclic anthraquinone processes for producing peroxide. However, these tetrahydroanthraquinones are prepared by the catalytic reduction of the parent anthraquinone and significant anthraquinone losses can occur in this step.

SUMMARY OF THE INVENTION

An improved route by which tetrahydroanthraquinones can be produced in high yields has been developed in which a compound of the formula

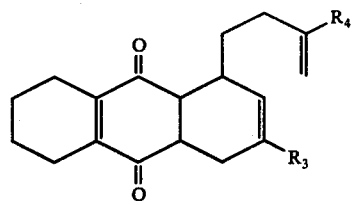

is oxidized in the presence of molecular oxygen, from 0.1% to 25% by weight based on the starting compound of a strong organic base and optionally a solvent at a temperature of from 20° to 100° C.

Surprisingly, under these conditions, the tetrahydro compound (III) is produced in high yields. Substantially none of the fully aromatic anthraquinone (V),

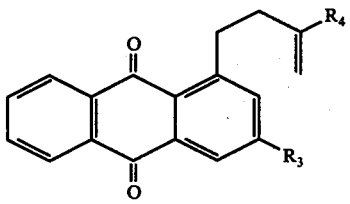

which is less desirable for the purpose of manufacturing hydrogen peroxide, is produced.

The 5,6,7,8-tetrahydro-1-alkenyl-9,10-anthraquinone that results from the process of this invention may be used directly in the anthraquinone process for the production of hydrogen peroxide or the side chain of the 1-alkenyl tetrahydroanthraquinone may be catalytically reduced to yield a 1-alkyl tetrahydroanthraquinone.

The 1-alkenyl tetrahydroanthraquinone product resulting from the process of this invention is highly soluble in the solvents employed in the production of hydrogen peroxide and are therefore extremely useful for the production of hydrogen peroxide. More importantly, however, the yields of the 1-alkyl tetrahydroanthraquinones obtained with the product resulting from the process of this invention are superior to those obtained by the catalytic reduction of the parent anthraquinone.

DETAILED DESCRIPTION OF THE INVENTION

The starting compound for the process of this invention is prepared by condensing 5,6,7,8-tetrahydro-1,4-naphthoquinone in a Diels-Alder reaction with a triene of the formula

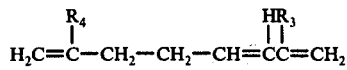

wherein $R_3$ and $R_4$ are the same or different and can be an alkyl group having one to eight carbon atoms or hydrogen.

The reaction sequence by which anthraquinones are prepared from the triene through the process of this invention is as follows:

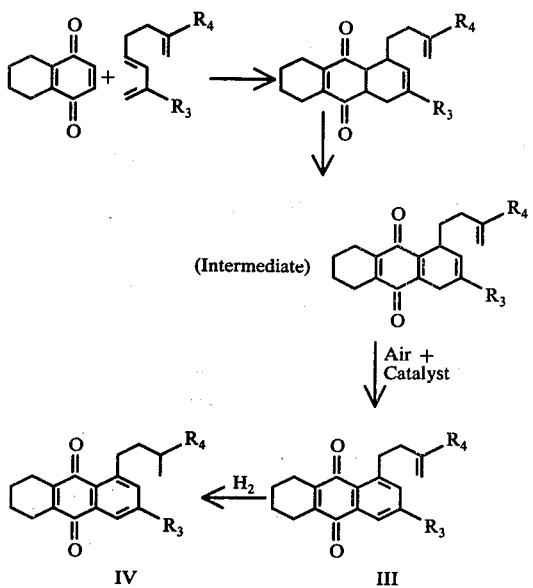

(Intermediate)

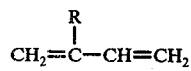

wherein $R_3$ and $R_4$ are the same or different and can be an alkyl group having one to eight carbon atoms (e.g., methyl, ethyl, propyl, butyl, amyl, hexyl, heptyl, octyl and isomers thereof) or hydrogen.

The compounds of formula III are a new class of compounds which can be used directly to produce hydrogen peroxide. In such a case, a solution of III is catalytically reduced and absorbs two equivalents of hydrogen in the first hydrogenation cycle. One equivalent of hydrogen reduces the quinone system to the hydroquinone in the usual way while the other saturates the double bond in the side chain. Oxidation of the hydroquinone produces hydrogen peroxide and tetrahydroanthraquinone according to the following reaction sequence:

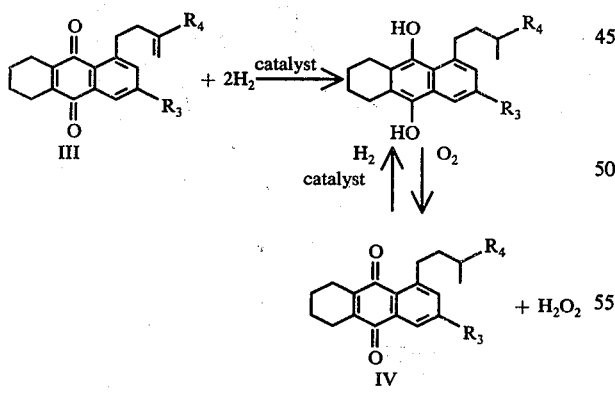

In all subsequent cycles, quinone IV absorbs the usual one equivalent of hydrogen and forms the hydroquinone. In practical terms, this discovery is important since reaction product III need not be converted to compound IV in a separate manufacturing step since tetrahydroanthraquinone III can be added directly to a plant hydrogenator where the double bond is saturated concurrently with the reduction of the quinone system in the production of hydrogen peroxide.

Alternatively, however, reaction product III can be hydrogenated in the presence of a catalytic amount of hydrogenation catalyst to saturate the side chain before it is introduced into the system for the preparation of hydrogen peroxide. In either case, a high yield of compounds III and IV is obtained by the improved process of this invention.

The alkyl substituted triene starting materials for the Diels-Alder condensation may be prepared by a process described in U.S. Pat. No. 3,888,890. In said patent, the starting triene is prepared by (A) homodimerizing a monoalkyl butadiene of the formula $$CH_2=\overset{\overset{R}{|}}{C}-CH=CH_2$$

or (B) codimerizing (a) 1,3-butadiene and a monoalkyl butadiene, or (b) two different monoalkyl butadienes in the presence of a catalytic amount of a dienophile-coordinated palladium-phosphine complex catalyst.

The Diels-Alder condensation reaction in which the above-described starting materials are employed is carried out at a temperature of from about 25° to 150° C. until the desired degree of condensation is achieved. The preferred reaction temperature ranges from about 75° to 125° C. The starting materials are generally employed in approximately equimolar proportions although either may be used in excess. Ordinarily, separation of the adduct from the reaction mixture will not be necessary.

In the process of this invention the condensation adduct is oxidized in the presence of molecular oxygen, preferably air, at a temperature ranging from about 0° to 150° C., preferably from 20° to 100° C.

The strong organic base catalyzes the oxidation process of this invention. The strong organic base may be (1) diazabicyclo compounds such as 1,5-diazabicyclo[4.3.0]non-5-ene (DBN),
1,5-diazabicyclo[5.4.0]undec-5-ene (DBU),
1,4-diazabicyclo[2.2.2]octane;

(2) quaternary ammonium hydroxides such as tetramethylammonium hydroxide and the like; (3) trialkylamines such as, for example, N,N-diethylcyclohexylmine,
N,N-diisopropylethylamine,
N,N-dimethylbenzylamine,
tribenzylamine,
tributylamine,
triethylamine,
trimethylamine,
tripropylamine,
tri-n-octylamine,
quinuclidine,
1,8-bis-(dimethylamino)-naphthalene,
N,N-dimethyl-t-butylamine,
1,4-dimethylpiperazine,
N-ethyldibenzylamine,
tridodecylamine,
N,N-dimethylcyclohexylamine, and (4) mixtures thereof.

Any amount of the strong organic base that is sufficient to catalyze the oxidation of the Diels-Alder reaction product to the tetrahydroanthraquinone may be used. Preferably from about 0.1% to about 25% by weight based on the weight of the Diels-Alder reaction product is used, most preferably 0.5% to 5%.

The oxidation of the Diels-Alder reaction product with molecular oxygen in the presence of the aforesaid organic base readily converts such compounds to 1-alkenyl tetrahydroanthraquinones III.

The process of this invention may or may not be carried out in the presence of a solvent. The solvent may also be referred to as a diluent. It is, however, preferred that a solvent be used. The presence of a solvent or diluent of an alcohol such as methanol or ethanol; a ketone such as acetone or methyl ethyl ketone; an ester such as ethyl acetate or a hydrocarbon such as benzene or cyclohexane or mixtures thereof are preferred.

As stated hereinbefore, the reaction product obtained at this point (compound III) can be used directly in the production of hydrogen peroxide. Alternatively, compound III can be hydrogenated in the presence of a hydrogenation catalyst to saturate the 1-alkenyl group before being thus employed. In the latter case, compound III is hydrogenated to compound IV.

When compounds III and/or IV are used directly in the hydrogen peroxide manufacturing system, they exhibit excellent solubilities in essentially all of the water immiscible solvents or solvent mixtures commonly regarded as suitable in formulating working solutions. The solubilities in such solvents of the anthrahydroquinone forms of these compounds are particularly outstanding. Since in cyclic anthraquinone hydrogen peroxide processes, the maximum permissible concentration of the working intermediate is limited by the solubility of its anthrahydroquinone form, the significance of the high solubilities of the anthrahydroquinone forms are readily apparent.

Said working solutions can be formulated by dissolving one or more of tetrahydroanthraquinones III and/or IV in any of the water immiscible solvents or mixtures of solvents commonly used in preparing such working solutions. These usually will consist of mixtures of solvents, one of which is a good solvent for the anthraquinone form of the intermediate and one which is a good solvent for the anthrahydroquinone form.

As a matter of fact, the anthrahydroquinone forms of the 1-alkyl tetrahydroanthraquinones are sufficiently soluble in those solvents which are normally regarded as solvents for the anthraquinone forms of the intermediates that high peroxide synthesis capacity working solutions can readily be formulated using working solvents such as xylene, trimethylbenzene and methylnaphthalene as sole solvents, i.e., in the absence of any solvent of the type normally used in solvent mixtures as solvents for the anthrahydroquinone form.

The invention is illustrated by the following examples in which all parts, proportions and compositions expressed as percentages are by weight, unless stated otherwise.

EXAMPLE 1

(Preparation of Starting Compound)

1-(3-Butenyl)-1,4,1a,4a,5,6,7,8-Octahydroanthraquinone

A mixture of 35 grams (0.216 mole) of tetrahydronaphthoquinone and 27 grams (0.25 mole) of 1,3,7-octatriene in 100 ml heptane was refluxed for 18 hours. The solution was treated with powdered charcoal, filtered and slowly cooled. At $-40°$ C., 49.9 g (85% yield) of crude product precipitated and was collected on a sintered glass filter. A 4.9 g analytical sample, after recrystallization from methanol, had a mp of 45° to 46° C.

Anal. Calcd. for $C_{18}H_{22}O_2$: C, 79.96%; H, 8.20%. Found: C, 80.04%; H, 7.74%.

In the NMR spectrum of the product ($CCl_4$), signals occurred at 5.3 to 5.9 (multiplets, 3H), 4.7 to 5.2 (multiplets, 2H), 2.9 to 3.4 (multiplets, 2H), and 1.2 to 2.7 ppm (complex multiplets, 15H).

EXAMPLE 2

(Preparation of Starting Compound)

Tetrahydronaphthoquinone - Isoprene Dimer Adduct

A solution of 101 g (0.623 mole) of tetrahydronaphthoquinone and 110 g (0.81 mole) of 2,7-dimethyl-1,3,7-octatriene in 300 ml cyclohexane was refluxed for 18 hours. After removal of 200 ml solvent, 300 ml of hexane were added. The mixture was then warmed, stirred with powdered charcoal, and filtered. On cooling, 151.3 g of crude product were obtained (81.5% yield). A 3 g analytical sample, after recrystallization from 20 ml hexane, had a mp of 87.5° to 88° C.

Anal. Calcd. for $C_{20}H_{26}O_2$: C, 80.49%; H, 8.78%. Found: C, 80.86%, H, 8.57%.

In the NMR spectrum ($CDCl_3$), signals occurred at 5.48 (broad singlet, 1H), 4.62 (multiplet, 2H), 3.0 to 3.4 (multiplet, 2H) and 1,4 to 2.6 ppm (complex multiplets, 21H).

EXAMPLE 3

1-(3-Butenyl)-1,4,5,6,7,8-Hexahydroanthraquinone

A mixture of 13.8 g of tetrahydronaphthoquinone (0.085 mole) and 10 g (0.092.5 mole) of 1,3,7-octatriene was refluxed for 1½ hours in 100 ml of ethanol. After the addition of 1 ml of 1,5-diazabicyclo[4.3.0]non-5-ene (DBN), the mixture was stirred while exposed to air for 24 hours. The ethanol was then blown off and the residue was dissolved in benzene and chromatographed on acidic alumina. From the eluate, 11.2 g of crude product were obtained (49% yield). The crude product was rechromatographed on acidic alumina using a 3:1 mixture of cyclohexane/benzene as the eluent. After removal of the solvent, the product was recrystallized from methanol to yield an analytical product having a mp of 47° to 48° C.

Anal. Calcd. for $C_{18}H_{20}O_2$: C, 80.56%; H, 7.51%. Found: C, 80.53%; H, 7.49%.

In the NMR spectrum ($CDCl_3$), signals occurred at 5.4 to 6.0 (multiplets, 3H), 4.7 to 5.2 (multiplets, 2H), 3.45 (multiplet, 1H), 3.05 (multiplet, 2H), 2.2 to 2.7 (multiplet, 4H), and 1.3 to 2.0 ppm (multiplets, 8H).

EXAMPLE 4

1-(3-Butenyl)-5,6,7,8-Tetrahydroanthraquinone

A 45 g sample of the tetrahydronaphthoquinone-butadiene dimer adduct of Example 1 was dissolved in 400 ml THF and 20 drops of 1,5-diazabicyclo[4.3.0]non-5-ene were added. The solution was stirred for 65 hours while exposed to air. The THF was then blown off with air and the residue was dissolved in benzene. The benzene solution was filtered to remove insoluble impurities and the solution was then chromatographed on Florisil. The product was eluted with a 4:1 mixture of benzene/ethyl acetate, and the yield of crude product was 15 g (34% yield). An analytical sample, after recrystallization first from ethanol, then from hexane, had a mp of 111° to 113° C.

Anal. Calcd. for $C_{18}H_{18}O_2$: C, 81.17%; H, 6.81%. Found: C, 81.27%; H, 6.65%.

In the NMR spectrum ($CDCl_3$), signals occurred at 8.00 (quartet, 1H), 7.2 to 7.7 (multiplet, 2H), 5.5 to 6.2 (multiplet, 1H), 4.75 to 5.3 (multiplet, 2H), 3.24 (triplet, J = 7.5 cps, 2H), 2.1 to 2.8 (multiplet, 6H), and 1.4 to 2.0 ppm (multiplet, 4H).

EXAMPLE 5

1-(3-Isopentenyl)-3-Methyl-5,6,7,8-Tetrahydroanthraquinone

A 50 g sample of the tetrahydronaphthoquinone-isoprene dimer adduct of Example 2 was dissolved in 150 ml benzene. After the addition of 1 ml 1,5-diazabicyclo[4.5.0]non-5-ene, the mixture was vigorously stirred while exposed to air overnight. A second 1 ml sample of 1,5-diazabicyclo[4.3.0]non-5-ene was then added and the mixture stirred for an additional 6 hours. A 2 g sample of acidic alumina was then added to adsorb the basic catalyst and after 15 minutes stirring was removed by filtration. The solution was then chromatographed on acidic alumina using benzene as the eluate. The yield of crude product was 43.5 g (88%). A 5 g sample was recrystallized first from 50 ml methanol, then from 40 ml hexane to give an analytical product of mp 75° to 75.5° C.

Anal. Calcd. for $C_{20}H_{22}O_2$: C, 81.60%; H, 7.53%. Found: C, 81.83%; H, 7.44%.

In the NMR spectrum of the product ($CCl_4$), signals occurred as 7.60 (singlet, 1H), 1.12 (singlet, 1H), 4.70 (broad singlet, 2H), 3.11 (triplet, J = 8.0 cps, 2H), and 1.5 to 2.7 ppm (complex multiplets, 16H).

EXAMPLE 6

1-n-Butyl-5,6,7,8-Tetrahydroanthraquinone

A 5 g sample of 1-(3-butenyl)-5,6,7,8-tetrahydroanthraquinone was dissolved in 150 ml of ethyl acetate and hydrogenated using 0.25 g of 10% Pd/charcoal as the catalyst. Hydrogen uptake stopped sharply after absorption of two equivalents of hydrogen and the solution was then filtered and oxidized with air. The solvent was then blown off with air and the residue recrystallized from methanol to give 4.3 g of product (86% yield), mp 49° to 51° C.

Anal. Calcd. for $C_{18}H_{20}O_2$: C, 80.56%; H, 7.51%. Found: C, 80.56%; H, 7.32%.

In the NMR spectrum of the product ($CCl_4$) signals occurred at 7.80 (quartet, J = 7.0 and 2.5 cps, 1H), 7.20 to 7.55 (multiplets, 2H), 3.01 (broad triplet, J = 7.0 cps, 2H), 2.7 to 2.7 (complex multiplets, 4H), 1.2 to 1.9 (complex multiplets, 8H), and 0.92 ppm (broad triplet, 3H).

EXAMPLE 7

1-Isopentyl-3-Methyl-5,6,7,8-Tetrahydroanthraquinone

A 22.6 g sample of 1-(3-isopentenyl)-3-methyl-5,6,7,8-tetrahydroanthraquinone was dissolved in 125 ml of THF and hydrogenated at room temperature using 1 g of 5% Pd/C as the catalyst. The expected two equivalents of hydrogen were absorbed within 1 hour. After filtering, 1 ml of 1,5-diazabicyclo[4.3.0]non-5-ene was added and the mixture was stirred for 1½ hours while exposed to air. A 1 g sample of acidic alumina was then added to absorb the catalyst and after 15 minutes stirring was removed by filtration. The solvent was then blown off and the residue recrystallized from methanol to give 22.8 g of product (100% yield), mp 65° to 66° C. A mixed meeting point with an authentic sample prepared by reduction of the parent anthraquinone showed no depression, and infrared and NMR spectra of the two samples were identical.

EXAMPLE 8

Hydrogen Peroxide-Using 1-(3-Butenyl)-5,6,7,8-Tetrahydroanthraquinone

A 1 g sample of the anthraquinone was dissolved in 10 ml of xylene and hydrogenated using 0.52 g of a $Pd/Al_2O_3$ catalyst containing 0.45% metallic palladium. Over a 45 minute period, the solution absorbed 2.02 equivalents of hydrogen and uptake ceased at that point. The solution was then filtered to remove the catalyst and was oxidized with oxygen. During the oxidation, 50 ml of water were added to extract the hydrogen peroxide produced. After the oxidation was complete, the aqueous layer was withdrawn in a separatory funnel and the organic solution was then extracted twice again with 25 ml portions of water. Titration of the extracted hydrogen peroxide with a ceric ammonium sulfate solution showed the yield to be 91% of theory.

In two subsequent runs with the same solution, conducted in a manner similar to that described above, approximately 1 equivalent of hydrogen was absorbed in each case. Yields of hydrogen peroxide were 99% and 100%.

To confirm the identity of the anthraquinone, most of the solvent was then removed on the steam bath and the residue was chromatographed on alumina using benzene as the eluent. The yellow fraction containing the anthraquinone was blown to dryness with a stream of air, and the product was then recrystallized from methanol. This sample had a melting point of 48° to 49° C. A mixed melting point with an authentic sample of 1-n-butyl-5,6,7,8-tetrahydroanthraquinone showed no depression, and infrared spectra of the two samples were identical.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. A process for the preparation of a 5,6,7,8-tetrahydro-1-alkenyl-9,10-anthraquinone which comprises oxidizing a starting compound of the formula

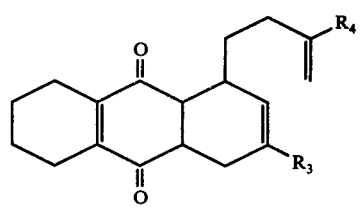

where $R_3$ is an alkyl group of 1 to 8 carbon atoms or hydrogen and $R_4$ is an alkyl group of 1 to 8 carbon atoms or hydrogen at from 20° to 100° C. in the presence of molecular oxygen, from 0.1% to 25% by weight based on the starting compound of a strong organic base and optionally a solvent.

2. The process of claim 1 wherein the organic base is 1,5-diazabicyclo[4.3.0]non-5-ene.

3. The process of claim 1 wherein the organic base is 1,5-diazabicyclo[5.4.0]undec-5-ene.

4. The process of claim 1 wherein the amount of organic base is 0.5% to 5%.

5. The process of claim 4 wherein the organic base is 1,5-diazabicyclo[4.3.0]non-5-ene.

6. The process of claim 4 wherein the organic base is 1,5-diazabicyclo[5.4.0]undec-5-ene.

7. The process of claim 1 wherein a solvent is present.

8. The process of claim 7 wherein the solvent is ethanol.

9. The process of claim 8 wherein the organic base is 1,5-diazabicyclo[4.3.0]non-5-ene.

10. The process of claim 8 wherein the organic base is 1,5-diazabicyclo[5.4.0]undec-5-ene.

11. The process of claim 7 wherein the solvent is methanol.

12. The process of claim 11 wherein the organic base is 1,5-diazabicyclo[4.3.0]non-5-ene.

13. The process of claim 11 wherein the organic base is 1,5-diazabicyclo[5.4.0]undec-5-ene.

14. The process of claim 7 wherein the solvent is ethyl acetate.

15. The process of claim 14 wherein the organic base is 1,5-diazabicyclo[4.3.0]non-5-ene.

16. The process of claim 14 wherein the organic base is 1,5-diazabicyclo[5.4.0]undec-5-ene.

* * * * *